US012755828B1

(12) United States Patent
Van Wilt et al.

(10) Patent No.: US 12,755,828 B1
(45) Date of Patent: Oct. 6, 2026

(54) RECOMMENDATION METHODS, SYSTEMS AND DEVICES

(71) Applicant: Cornell Tech JCTI, New York, NY (US)

(72) Inventors: Yasmine Van Wilt, New York, NY (US); Kenneth Bahk, Glenview, IL (US)

(73) Assignee: The Joan and Irwin Jacobs Technion-Cornell Institute, New York, NY (US)

( * ) Notice: Subject to any disclaimer, the term of this patent is extended or adjusted under 35 U.S.C. 154(b) by 111 days.

(21) Appl. No.: 18/315,457

(22) Filed: May 10, 2023

Related U.S. Application Data

(63) Continuation of application No. 16/735,610, filed on Jan. 6, 2020, now Pat. No. 11,694,786.
(Continued)

(51) Int. Cl.
*G16H 20/70* (2018.01)
*A61M 21/02* (2006.01)
(Continued)

(52) U.S. Cl.
CPC ............ *G16H 20/70* (2018.01); *A61M 21/02* (2013.01); *G06F 16/435* (2019.01); *G06N 3/004* (2013.01); *G06N 5/04* (2013.01); *G06Q 20/123* (2013.01); *G06Q 30/0203* (2013.01); *G06Q 30/0204* (2013.01); *G06Q 30/0631* (2013.01); *G06Q 50/265* (2013.01); *G16H 10/20* (2018.01); *G16H 10/60* (2018.01); *G16H 15/00* (2018.01); *G16H 20/60* (2018.01); *G16H 70/20* (2018.01); *A61M 2021/0027* (2013.01); *A61M 2021/005* (2013.01)

(58) Field of Classification Search
CPC ........ G16H 20/70; G16H 10/60; G16H 15/00; G16H 10/20; G16H 20/60; G16H 70/20; G06F 16/435; A61M 21/02; G06N 3/004; G06N 5/04; G06Q 20/123; G06Q 30/0203
USPC .......................................................... 705/2–3
See application file for complete search history.

(56) References Cited

U.S. PATENT DOCUMENTS 8,683,348 B1 * 3/2014 Blank ..................... G06F 3/038 715/709
10,943,407 B1 * 3/2021 Morgan ................. G16H 15/00
(Continued)

FOREIGN PATENT DOCUMENTS

WO WO-2018100330 A1 * 6/2018 ........... A61B 5/4836

*Primary Examiner* — Michael Tomaszewski
(74) *Attorney, Agent, or Firm* — M&B IP Analysts, LLC

(57) ABSTRACT

Some embodiments of the present disclosure relate to systems, devices, and methods for making recommendations to users for, individually or together, goods, services, and information/media (e.g., audio, video, publications), as well as verifying the veracity of data/information, based upon an emotional impact of such goods/services and/or media/information on the user, other users, and/or other individuals, as well some embodiments directed to systems, devices, and methods for treating one or more brain functions, including neurological conditions and episodes associated therewith by determining (and optionally providing) media (e.g., audio, but in some embodiments, any of audio, textual information, and video), which may be referred to as optimal medical media ("OMM").

10 Claims, 6 Drawing Sheets

Related U.S. Application Data

(60) Provisional application No. 62/788,908, filed on Jan. 6, 2019, provisional application No. 62/788,656, filed on Jan. 4, 2019.

(51) Int. Cl.

| | |
|---|---|
| ***G06F 16/435*** | (2019.01) |
| ***G06N 3/004*** | (2023.01) |
| ***G06N 5/04*** | (2023.01) |
| ***G06Q 20/12*** | (2012.01) |
| ***G06Q 30/0203*** | (2023.01) |
| ***G06Q 30/0204*** | (2023.01) |
| ***G06Q 30/0601*** | (2023.01) |
| ***G06Q 50/26*** | (2012.01) |
| ***G16H 10/20*** | (2018.01) |
| ***G16H 10/60*** | (2018.01) |
| ***G16H 15/00*** | (2018.01) |
| ***G16H 20/60*** | (2018.01) |
| ***G16H 70/20*** | (2018.01) |
| *A61M 21/00* | (2006.01) |

(56) References Cited

U.S. PATENT DOCUMENTS

| | | | | |
|---|---|---|---|---|
| 11,694,786 | B1 * | 7/2023 | Van Wilt ................ | G16H 20/60 600/27 |
| 2007/0016096 | A1 * | 1/2007 | McNabb ................ | A61B 5/372 600/545 |
| 2013/0297536 | A1 * | 11/2013 | Almosni ................ | G16H 50/20 706/12 |
| 2014/0039975 | A1 * | 2/2014 | Hill ........................ | A61B 5/167 705/7.29 |
| 2014/0323817 | A1 * | 10/2014 | el Kaliouby ........... | G16H 20/40 600/300 |
| 2015/0286627 | A1 * | 10/2015 | Chang ................... | G06F 40/205 704/9 |
| 2015/0348122 | A1 * | 12/2015 | Cornell .............. | G06Q 30/0261 705/14.58 |
| 2015/0348162 | A1 * | 12/2015 | Morris ............... | G06Q 30/0631 705/26.7 |
| 2017/0083927 | A1 * | 3/2017 | Niedziela ........... | G06Q 30/0201 |
| 2017/0235912 | A1 * | 8/2017 | Moturu .................. | G16H 40/67 705/2 |
| 2017/0352283 | A1 * | 12/2017 | Lau ........................ | A61B 5/165 |
| 2018/0020963 | A1 * | 1/2018 | Friant ................ | G06Q 30/0269 705/14.66 |
| 2018/0096740 | A1 * | 4/2018 | Moturu .................. | G16H 50/50 |
| 2018/0253662 | A1 * | 9/2018 | Booch .................... | G06N 20/00 |
| 2019/0019507 | A1 * | 1/2019 | Abrahams ................ | G06N 5/04 |
| 2019/0189259 | A1 * | 6/2019 | Clark ..................... | G16H 10/60 |
| 2019/0205469 | A1 * | 7/2019 | Cunico .............. | G06Q 30/0271 |
| 2019/0318008 | A1 * | 10/2019 | Cruz Huertas ..... | G06F 16/4387 |

* cited by examiner

RECOMMENDATION METHODS, SYSTEMS AND DEVICES

RELATED APPLICATIONS

The subject application is a continuation of U.S. patent application Ser. No. 16/735,610, filed Jan. 6, 2020 which claims benefit of and priority to U.S. provisional patent application Nos. 62/788,656, filed Jan. 4, 2019, and 62/788,908, filed Jan. 6, 2019, each disclosure of which is herein incorporated by reference in its entirety.

FIELD OF THE DISCLOSURE

Some embodiments of the present disclosure relate to systems, devices, and methods for making recommendations to users for, individually or together, goods, services, and information/media (e.g., audio, video, publications), as well as veracity of data/information, based upon an emotional impact of such goods/services and/or media/information on the user, other users, and/or other individuals, as well some embodiments directed to systems, devices, and methods for treating one or more brain functions, including neurological conditions and episodes associated therewith by determining (and optionally providing) media (e.g., audio, but in some embodiments, any of audio, textual information, and video), which may be referred to as optimal medical media (“OMM”).

BACKGROUND

The efficacy of recommendation systems and methods, and the field of psychographics, have evolved to improve our ability to match the right product/service/item with the right customer/user. While this practice has extended into media, systems employing such functionality leave much to be desired, as such systems function so as to selecting media of a certain genre that either the listener/viewer/user has preselected, or, the system monitors the listener/viewer/user’s past selections, and presents similar selections to respective listeners/viewers/users. Moreover, present recommendation systems/methods for product/service need improvement.

SUMMARY OF AT LEAST SOME OF THE EMBODIMENTS

Group I

Group I embodiments are directed to systems, devices, and methods for making recommendations to users for, individually or together, goods, services, and information/media (e.g., audio, video, publications) based upon an emotional impact of such goods/services and/or media on the user, other users, and/or other individuals, as well as embodiments directed to methods, systems and devices for determining the veracity of media information (e.g., news) based upon emotional impact of such media upon one or more other users and/or individuals (similarly, “other users” and “other individuals” may be persons having similar personality type, background, gender, age, geographic location, and the like, for (example).

Accordingly, some Group I embodiments of the present disclosure are directed to systems, devices, and methods for market analytics and/or user recommendation of digital information (for example). Accordingly, in some embodiments, such a market analytics/user recommendation methods comprise identifying one or more correlations between at least one of one or more sentient agents and one or more non-sentient agents associated with corresponding systems, determining at least one psychometric profile for each, the psychometric profile comprising an Emotional Impact Factor (EIF), and determining at least one market, and/or at least one recommendation for at least one of information, product, and service, using each EIF, for at least one user. Such embodiments may further include providing the at least one market and/or recommendation to at least one user.

Such embodiments (as well as others) may include one and/or another, and in some embodiments a plurality, and in some embodiments, all of the following additional features, functions, steps, structure, and clarifications, leading to yet further embodiments:

- determining the EIF may comprise connecting a plurality of data points,
  - the connecting may be configured for identifying at least one parameter;
    - the at least one parameter including anthropological, ethnographic, and psycho-social factors;
- determining the EIF may include integrating and/or weighting of the one or more parameters, and/or integrating and/or weighting of the one or more additional factors;
- determining the EIF may comprise or may further comprise at least one of: text-based analysis of annotations of songs, indexing, media analysis, and principle component analysis;
- determining the EIF may comprise or may further comprise examining structured or unstructured behavior data of at least one user;
  - such structured or unstructured data may be from one or more defined networks and/or systems, where the defined networks and/or systems may comprise at least one of: streaming services, platforms, and peer-to-peer networks;
- a respective EIF may be determined through an analysis of a limited number of parameter, for example, n>12 parameters;
- the EIF may be configured for use with a media recommendation system, where, for example, the media recommendation system may comprise a sales recommendation system configured to match at least one product with the at least one user;
- the one or more parameters may comprise at least one of: previous consumption within a given recommendation system, one or more platforms, and one or more peer-to-peer network transactions over a predetermined period of time;
- weighting of the one or more parameters may comprise increasing weighting of the transactions over the predetermined period of time;
- the EIF may be configured for use for at least one of analyzing, visualizing, and recommending media content for at least one user;
- and
- the one or more sentient agents may be configured to determine a relationship between at least one of a user’s: emotional quotient, psychometric profile, and the EIF of content available for consumption on a given media service, platform, and/or peer-to-peer network.

In some embodiments, a market analytics/user recommendation system is provided. Such a system, according to some embodiments, includes at least one processor having code operating thereon configured to cause the at least one processor to identify one or more correlations between at least one of one or more sentient agents and one or more non-sentient agents associated with corresponding systems, determine at least one psychometric profile for each, the psychometric profile comprising an Emotional Impact Factor (EIF), and determining at least one market, and/or at least one recommendation for at least one of information, product, and service, using each EIF for at least one user.

Such embodiments (as well as others) may include one and/or another, and in some embodiments a plurality, and in some embodiments, all of the following additional features, functions, steps, structure, and/or clarifications, leading to yet further embodiments:

- the code may be further configured to cause the at least one processor to provide the at least one market and/or recommendation to at least one user;
- the code for causing the at least one processor to determine the EIF may comprise code for causing the at least one processor to connect a plurality of data points, where connecting may be configured for identifying at least one of anthropological, ethnographic, and psycho-social factors;
- the code for causing the at least one processor to determine the EIF may include code to cause the at least one processor to integrate and/or weight the one or more parameters, and/or integrate and/or weight the one or more additional factors;
- the code for causing the at least one processor to determine the EIF comprises or further comprises code for causing the at least one processor to textually analyze annotations of songs, indexing, media analysis, and principle component analysis;
- the code for causing the at least one processor to determine the EIF may comprise or may further comprise code for causing the at least one processor to examine structured or unstructured behavior data of at least one user;
  - where the structured or unstructured data may be from one or more defined networks and/or systems;
  - the defined networks and/or systems may comprise at least one of: streaming services, platforms, and peer-to-peer networks;
- the code for causing the at least one processor to determine the EIF may include code for causing the at least one processor to determine a respective EIF via an analysis of a plurality or parameters, and in some embodiments, such "n" parameters may be greater than 12;
- a media recommendation system;
  - the media recommendation system may comprise a sales recommendation system configured to match at least one product with at least one user;
- the one or more parameters may comprise at least one of: previous consumption within a given recommendation system, one or more platforms, and one or more peer-to-peer network transactions over a predetermined period of time;
- weighting of the one or more parameters may comprise increasing weighting of the transactions over the predetermined period of time;
- the EIF may be configured for use for at least one of analyzing, visualizing, and recommending media content for at least one user;
- the one or more sentient agents may be configured to determine a relationship between at least one of a user's: emotional quotient, psychometric profile, and the EIF of content available for consumption on a given media service, platform, and/or peer-to-peer network;
- the at least one processor may comprise at least one networked server;
- the at least one processor may comprise at least one client computer;
- and
- the system may further comprise at least one mobile device in wired or wireless communication with the at least one processor;
  - where the at least one mobile device may comprise a plurality of mobile devices each associated with a particular user (for example).

Some embodiments of the present disclosure are directed to systems, devices, and methods for a false-media identification method. Such embodiments comprise reviewing one or more pieces of media, where each piece of media includes a source, determining at least one emotional impact factor (EIF) for each piece of media, and associating each EIF is a number or alphanumeric. The number or alphanumeric corresponds to a falseness scale, such that, in some embodiments, upon the associated EIF being greater than a predetermined threshold on the scale, the media may be flagged as false (or true, or presented to one or more users/viewers as a scale of veracity or falseness).

In some such embodiments:

- determining the EIF may be configured for a specific audience, where the audience may be one based on, for example, at least one of socio-economic status and educational level; and/or
- the method may further include notifying consumers of the one or more pieces of media of flagged false media Such method embodiments may be embodied in a device and/or system comprising at least one processor having code operating thereon configured to cause the at least one processor to perform the methodology above, as well as a mobile application configured for operation on, used or in combination with a mobile application and/or device. Moreover, such a mobile application may be configured to at least one of send, receive, and/or process information from the at least one processor according to the disclosed system embodiments. See General Embodiments below.

In some embodiments, data collected (and thus stored), and any other data associated with one or more users, individuals, and agents, and the like, can be used by an artificial intelligence (AI) component of the systems and methods disclosed. For example, such data can be used to train the AI to identify and/or interact with the sentient and/or non-sentient agents, and/or trained to determine either EIFs and/or recommendations. In some embodiments, the AI component may include interaction with an AI bot (AIB) by users and/or agents.

Group II

Group II embodiments are directed to systems, devices, and methods for treating one or more brain functions, including neurological conditions and episodes associated therewith.

Accordingly, in some such embodiments, a brain function medical treatment method comprising at least one of receiving first data corresponding to input from at least one patient (user) with respect to answers to a series questions (Q&A) during a period at which the at least one user is not experiencing an episode or a condition associated with at least one brain function, and selecting, by the at least one user, at least one medical media parameter. As a result of at least one of the first data, user selection, and interactive artificial intelligence (AI), where the AI optionally comprises or includes interaction with an AI bot (AIB), identifying OMM configured to counteract the at least one user experiencing the episode or the condition from entering at least one of a fugue state and a dissociative state. The method may also include, in some embodiments, repeating the previous steps.

Such embodiments, as well as others, may further comprise one and/or another (and in some embodiments, a plurality of, and in some embodiments, all of) of the following features, clarifications, functionality, steps, and structure, yielding yet further embodiments:

- the OMM may be configured as a treatment or well-being plan for treating the episode or condition;
- the OMM may be configured as at least one of one or more musical pieces, videos, and readings;
  - the at least one of the one or more musical pieces, videos, and readings may be configured as at least one playlist;
  - the at least one playlist is configured to treat a specific episode or condition;
  - the condition is selected from the group consisting of: distress, flow-state, weight-loss, and concentration;
- playing the OMM for/by the user for treatment of the at least one episode or condition;
- the OMM may be configured with a guiding component;
- determining the efficacy of the OMM with respect to the at least one episode or condition;
- providing feedback information on use of the OMM for treatment of the at least one episode or condition by at least one of the user, a medical professional, and the AIB;
- tracking secondary information;
  - the secondary information may comprise at least one of health data, and personal data;
  - health data may comprise at least one of heartrate, blood pressure, and temperature;
  - the personal data may comprise at least one of caloric intake, exercise data, sleep data, and fluid intake data;
  - and
  - feedback information may include alerts to users, suggestions of different media and combinations thereof, recommendations to connect with their physicians, historical user consumption, and the like;
- producing a report, where the report may include data collected, analyzed and/or determined;
- collecting medication data of the at least one user, where the medication information can comprise information related to pharmaceutical use;
- training the AI using at least one of user selection of parameters, feedback information, the secondary information, and medication information;
- identifying an emergency or potential emergency;
  - such emergencies may be identified by aberrations in user-behavior;
- recognizing patterns for the at least one user so as to identify trends in the at least one user with respect to selection of specific words indicative of a neurological condition;
  - the condition can be any of (for example) anxiety disorders, mood disorders, personality disorders, stress, and general health or wellness;
- the episode is a measurable or self-identified psycho-physical disease or discomfort;
- notifying at least one of the user and one or more individuals associated with the at least one user, regarding, the identification of any of a condition, episode, and behavior;
  - notifying comprises at least one of email, text, phone, and/or any method of secure direct in-application communication;
- secondary information, which may comprise at least one of: heart information, activity information, meal information, fluid-intake information;
- determining, based on at least the secondary information, whether the at least one user is within or outside of a state;
- the state may comprise, for example, a flow state or an emergency state;
- providing or associated an account for each of the at least one users;
  - for such accounts, collecting or aggregating funds for each account from a third party;
  - the third party may comprise an insurance provider;
  - the funds may comprise at least one incentive, where the incentive may comprise goods, services, and/or monetary compensation;
- selling data collected, analyzed, and/or otherwise produced by the method;
- using the OMM so as to train the at least one user to develop new habits through behavior modification;
  - training, for the at least one user, may comprise at least one of centering, practicing neuro-feedback, and mindfulness, then returning to a state of productivity;
- delay a length of time treatment of the at least one of the neurological episode and condition;
- configured the method to, in the at least one user, at least one of allay a fugue state, a panic attack, and achieve a dopaminergic state;
- a playlist may comprise a plurality of playlists each corresponding to a type including one or more of the following characteristics: variation of time signature, absence of minor keys, instrumentation, e.g., organic instrumentation (that is, non-modified via electronics, for example, acoustic instrumentation), variation of instrumentation, absence of dissonance, balanced audio recording, limitation of decibel level, pre-set decibel level, familiarity, length of play, continuous play, intermission length, dopaminergic effect, and anxiolytic effect;
- manipulation of the OMM by at least one of the at least one user and a medical professional;
- using the AI in creating at least one modifiable STEM for at least one media of the OMM;
  - the modifiable STEM may be modifiable by the at least one user;
  - the STEM may be modifiable via the key;
- the OMM comprises at least one song and includes a video component comprising lyrics corresponding to the at least one song configured such that the at least one user can sing the song;
- the OMM may be derived or otherwise based on recorded compositions from Baroque, classical, and neoclassical periods;
  - the compositions may be augmented;
- the AI at least partially configures the OMM;
- the configuring the medical media comprises remixing STEMs associated with the OMM;
- the OMM comprises at least one STEM, and wherein the STEM corresponds to a core element;

and the AI, after user selection of at least one parameter, composes and one or more pieces of the OMM;

composing the one or more pieces of the OMM may comprise remixing one or more STEMs associated with the OMM;

the at least one STEM may comprise a plurality of STEMs;

each STEM may correspond to a respective core element;

and the plurality of STEMs, and thus, core elements, configured to interact with one another to produce a desired affect, where, in some embodiments, the OMM is configured to produce the desired effect.

In some embodiments, a brain function medical treatment system is provided and comprises at least one processor having code operating thereon configured to cause the at least processor to receive first data corresponding to input from at least one patient (user) with respect to answers to a series questions (Q&A) regarding a period at which the at least one user is not experiencing an episode or a condition associated with at least one brain function, select, by the at least one user, at least one medical media parameter, operate as or access an interactive artificial intelligence (AI), wherein the AI optionally includes or is configured as an AI bot (AIB), and is configured to identify OMM configured to counteract the episode or the condition the at least one user experiences from entering at least one of a fugue state and a dissociative state, and optionally repeating one or more of receiving, selecting, and operating.

Such embodiments, as well as others, may further comprise one and/or another (and in some embodiments, a plurality of, and in some embodiments, all of) of the following features, clarifications, functionality, steps, and structure, yielding yet further embodiments:

the code may be further configured to cause the at least one processor to perform or otherwise conform with the one and/or another of the steps, functionality, or clarifications recited above with reference to the embodiments included in paragraph [0004];

the code may be further configured to cause the at least one processor to perform or otherwise conform; and the at least one of the at least one processor may comprise a server;

Systems according to some of the above-noted embodiments, may also, for example, include a mobile application configured for operation on, used or in combination with a mobile device. Moreover, such a mobile application may be configured to at least one of send, receive, and/or process information from the at least one processor. See General Embodiments below.

Group III Embodiments

Group III embodiments comprise any combination of systems, methods, and devices with respect to the above-noted embodiments (as well as any other embodiments disclosed herein), including, any combination of components, steps, structure, and functionality thereof.

Any of the above noted embodiments can be embodied in computer code operational on a computer (server, client, mobile, and the like) or computer system or platform, which causes the computer/platform to perform any and all of the noted methods disclosed, as well as non-transitory computer readable media. See, e.g., General Embodiments, below.

These and other embodiments, objects, and advantages of the various group of embodiments will become even more evident with reference to the associated drawings filed herewith and briefly described below, as well as the following detailed description for at least some of the embodiments.

DETAILED DESCRIPTION FOR AT LEAST SOME EMBODIMENTS

General Embodiments

Figure 1:
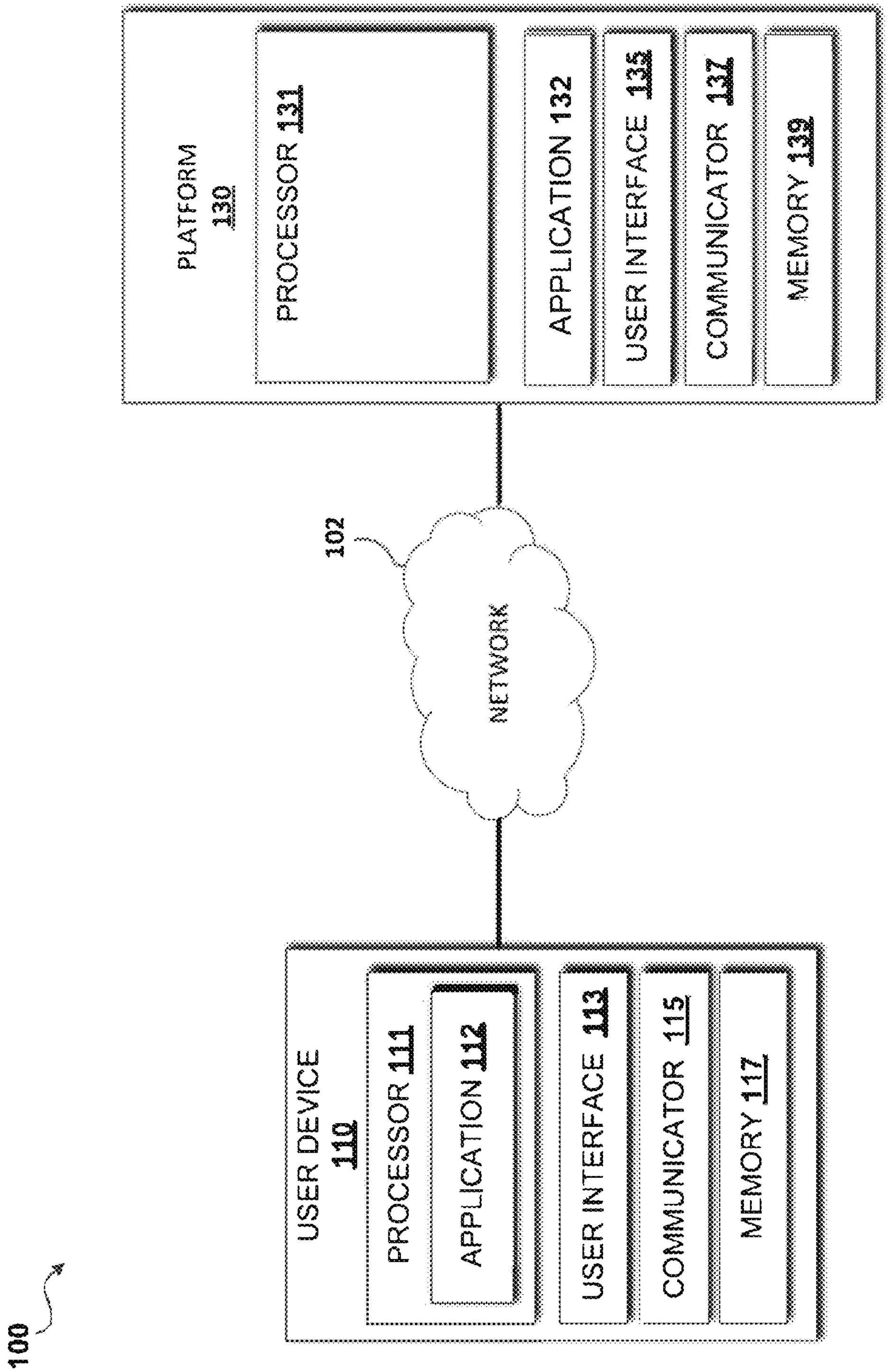
FIG. 1 is a functional block diagram depicting a general system (which in some embodiments, can be considered a device, and/or components of a system/device), according to some embodiments of the present disclosure.

FIG. 1 is a schematic block diagram depicting general device and system embodiments, configured to at least enable operation of the devices, systems and methods (and methods of Groups I-III operational thereon) according to at least some of the embodiments of Group I-III disclosed herein (see above, and below). To this end, as shown, system 100 can include user device 110 and platform 130 (e.g., recommendations platform), interconnected over network 102. While system 100 is shown as including two discrete devices, other arrangements can be contemplated (e.g., two or more discrete elements). Moreover, one and/or another of the functionalities of the various components of the user device and platform can be combined into a single device/system.

Network 102 can be or include, for example, an intranet, a local area network (LAN), a personal area network (PAN), a wireless local area network (WLAN), a wireless personal area network (WPAN), a wide area network (WAN) such as the Internet, a metropolitan area network (MAN), a world-wide interoperability for microwave access network (WiMAX®), an optical fiber (or fiber optic)-based network, a Wi-Fi™ network, a Bluetooth® network, a virtual network, and/or any combination thereof. Network 102 can include, for example, wired connections, wireless (e.g., radio communication, free-space optical communication) connections, fiber optic connections, and the like. Network 102 can include, for example, routers, firewalls, switches, gateway computers, edge servers, and the like. In some instances, network 102 can alternatively or otherwise include, for example, telecommunications, data communications, and/or data transmission channel, link, connection, or path, by which data and signals can be communicated, transmitted, or propagated between and amongst devices. For example, network 102 can include a near-field communications (NFC) connection (e.g., NFC beacon connection), a short-range or short-link communications connection (e.g., Bluetooth®), and/or the like. Network 102 can include any suitable combination of connections and protocols configured to enable and support interconnection, communications, and interoperations between user device 110 and platform 130.

User device 110 and platform 130 can individually and respectively include, for example, a device, node, system, or platform, such as a machine or compute device, compute system, compute platform, information system, programmable electronic device, information content processing device, and/or the like. For example, user device 110 and/or platform 130 can include, for example, a controller, a processor, a mobile phone, a smart phone, a tablet computer, a laptop computer, a personal or desktop computer, a server (e.g., database server), a virtual machine, a wearable device (e.g., electronic watch), an implantable device, and/or the like. User device 110 and/or platform 130 can otherwise be, include, or use any suitable type and combination of devices, systems, and/or platforms, capable of communicating or interoperating (e.g., via network 102) with one or more other devices, systems, and/or platforms, such as user device 110 and/or platform 130. In some embodiments, user device 110 and/or platform 130 may include internal and external hardware components, such as described with reference to FIG. 2. In other embodiments, user device 110 and/or platform 130 may be implemented in a cloud-computing environment, such as described with reference to FIGS. 3-4.

User device 110 includes processor 111, user interface 113, communicator 115, and memory 117. User device 110 can be configured to implement any suitable combination of devices and technologies, such as network devices and device drivers, to support the operation of processor 111, user interface 113, communicator 115, and memory 117, and provide a platform enabling communications (e.g., via network 102) between user device 110 and platform 130.

Processor 111 can be or include any suitable type of processing device configured to run and/or execute software, code, commands, or logic. For example, processor 111 can be or include a hardware-based integrated circuit (IC), a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC), or the like. Processor 111 can be operatively coupled to memory 117, such as by way of a data transfer device or system such as a bus (e.g., address bus, data bus, control bus). Processor 111 can otherwise include a processor configured to execute any suitable type or form of software, code, commands, and/or logic, corresponding to or representative of an application or program such as application 112, as described herein.

Application 112 (e.g., methodology of the embodiments of any of Groups I-III) can be or include any suitable type of application or program, such as a software or computer program, one or more subroutines contained in a program, an application programming interface, or the like. Application 112 can include any suitable type or form of software, code, commands, and/or logic representing instructions, such as machine-, computer-, or processor-executable code, logic, instructions, commands, and/or the like. Application 112 can be configured to reside or be hosted at user device 110. For example, application 112 can be configured be stored (e.g., via memory 117) at user device 110. Alternatively or in combination, application 112 can be configured to reside or be hosted at a device separate, distinct, or remote from user device 110, such as at a server, node, and/or the like. Application 112 can be configured to be run or executed by, at, or via any suitable type of processor or processing device, such as processor 111. For example, application 112 can be or include a native application, a web or web-based application, and/or a hybrid application (e.g., an application having a combination of native and web-based application characteristics or functionality).

User interface 113 can be or include any suitable type of user interface device configured to enable user interaction between a user and user device 110. In some embodiments, user interface 113 can be configured to enable user interaction between user (e.g., at user device 110) and platform 130, as described herein. For example, user interface 113 can be configured to provide (e.g., display) output (e.g., from application 132). Further, user interface 113 can be configured to receive user input (e.g., from a user at user device 110), as described herein. For example, user interface 113 can include one or more input devices such as a keyboard and mouse, and one or more output devices such as displays, screens, projectors, and the like. As another example, user interface 113 can include one or more input/output (I/O) devices, such as a touchscreen, a holographic display, a wearable device such as a contact lens display, an optical head-mounted display, a virtual reality display, an augmented reality display, and/or the like. User interface 113 can be configured to implement any suitable type of human-machine interface device, human-computer interface device, a batch interface, graphical user interface (GUI), and the like. User interface 113 can otherwise include or be configured to implement any suitable type of interface (e.g., user interface 113) capable of embodiment in conjunction with a device such as platform 130, such as to provide for user interaction between a user and the device, as described herein. In some embodiments, the user input received at user interface 113 can be sent (e.g., over network 102) to platform 130 for execution thereat.

Communicator 115 can be or include, for example, a hardware device operatively coupled to processor 111 and memory 117, and/or software stored in memory 117 and executable by processor 111, capable of enabling and supporting communications over a network (e.g., network 102) and/or directly between or among compute devices (e.g., user device 110 and platform 130), as well as devices for local alert (e.g., audible or visual signaling, via a speaker/headphone and screen or indicator light, respectively). For example, communicator 115 can be or include a network interface card (NIC), a network adapter such as a Transmission Control Protocol (TCP)/Internet Protocol (IP) adapter card or wireless communication adapter (e.g., a 4G wireless communication adapter using Orthogonal Frequency Division Multiple Access (OFDMA) technology), a Wi-Fi™ device or module, a Bluetooth® device or module, and/or any other suitable wired and/or wireless communication device. Communicator 115 can be configured to connect or interconnect user device 110 and one or more other devices (e.g., platform 130) for data communications therebetween, such as over a communications network (e.g., network 102). Communicator 115 can be configured to be implemented in conjunction with any suitable architecture, such as one designed for passing data and/or control information between processors (e.g., processor 111, processor 131), system memory (e.g., memory 117, memory 139), peripheral devices (e.g., user interface 113, user interface 135), and any other devices or components (e.g., of system 100 and/or including platform 130).

Memory 117 can be or include any suitable type of memory, data storage, or machine-, computer-, or processor-readable media capable of storing a machine or computer program, digital information, electronic information, and the like (e.g., of or associated with application 112). For example, memory 117 can be configured to store an application or program such as application 112, such as for execution by processor 111. Memory 117 can be or include a memory buffer, a hard drive, a magnetic disk storage device of an internal hard drive, magnetic tape, magnetic disk, optical disk, portable memory (e.g., flash drive, flash memory, portable hard disk, memory stick), a semiconductor storage device such as a random access memory (RAM) (e.g., RAM including cache memory), a read-only memory (ROM), an erasable programmable read-only memory (EPROM), an electrically erasable programmable read-only memory (EEPROM), and/or the like. Memory 117 can otherwise include any suitable type of memory or data storage, as such may be chosen as a matter of design.

Platform 130 includes, for example, processor 131, application 132 (which may be included as code residing on processor 131, and may be an application to perform, e.g., methodology of the embodiments of any of Groups I-III), user interface 135, communicator 137, and memory 139. Platform 130 can be configured to implement any suitable combination of devices and technologies, such as network devices and device drivers, to support the operation of processor 131, application 132, user interface 135, communicator 137, and memory 139, and provide a platform enabling communications (e.g., via network 102) between user device 110 and platform 130, as described herein. Platform 130 can be configured to make recommendations (e.g., via application 132). While platform 130 is shown as including certain discrete elements or components (e.g., processor 131, application 132, user interface 135, communicator 137, memory 139), other arrangements can be contemplated. For example, in some embodiments, platform 130 can alternatively or otherwise include processor 131, application 132, user interface 135, and memory 139, and/or any other number of discrete elements or components (e.g., including one or more integrated or separate devices, platforms, nodes, etc.), as such may be chosen as a matter of design. In some embodiments, the platform 130 can comprise a device, system, or platform such as a recommendations system according to the disclosed embodiments, Processor 131 can be or include any suitable type of processing device configured to run and/or execute software, code, commands, or logic. For example, processor 131 can be or include a hardware-based integrated circuit (IC), a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC), or the like. Processor 131 can be operatively coupled to memory 139, such as by way of a data transfer device or system such as a bus (e.g., address bus, data bus, control bus). Processor 131 can otherwise include a processor configured to execute any suitable type or form of software, code, commands, and/or logic, corresponding to or representative of an application or program such as application 132, as described herein.

Figure 2:
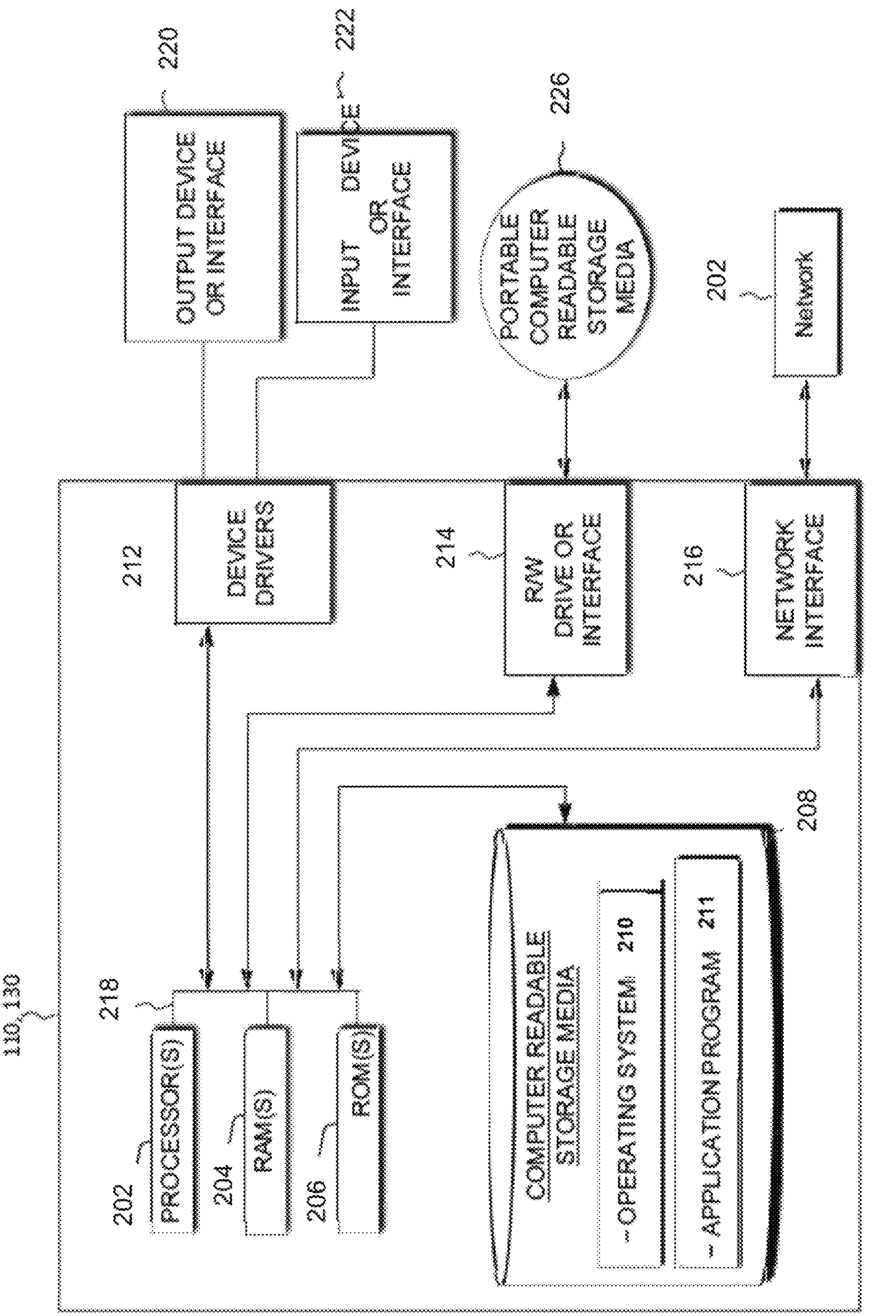
FIG. 2 is a block diagram depicting a user device and system, according to some embodiments, for performing/accomplishing methodology according to any of the embodiments of Groups I-III.

FIG. 2 is a block diagram depicting user device 110 and/or system 130, in accordance with some embodiments of the present disclosure. As shown, user device 110 and/or system 130 may include one or more processors 202 (e.g., microprocessors, CPUs, GPUs, etc.), one or more computer-readable RAMs 204, one or more computer-readable ROMs 206, one or more computer readable storage media 208, device drivers 212, read/write drive or interface 214, network adapter or interface 216, all interconnected over a communications fabric 218. The network adapter 216 communicates with a network 230. Communications fabric 218 may be implemented with any architecture designed for passing data and/or control information between processors (such as microprocessors, communications and network processors, etc.), system memory, peripheral devices, and any other hardware components within a system.

One or more operating systems 210 and one or more application programs 211 (e.g., those for performing at least some, and in some embodiments, all of the methodology of the embodiments of Groups I-III), such as secure application 132, residing on platform 130, are stored on one or more of the computer readable storage media 208 for execution by one or more of the processors 202 via one or more of the respective RAMs 204 (which typically include cache memory). In some embodiments, each of the computer readable storage media 208 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable medium (e.g., a tangible storage device) that can store a computer program and digital information.

User device 110 and/or system 130 may also include a read/write (R/W) drive or interface 214 to read from and write to one or more portable computer readable storage media 226. Application programs 211 on viewing device 110 and/or user device 120 may be stored on one or more of the portable computer readable storage media 226, read via the respective R/W drive or interface 214 and loaded into the respective computer readable storage media 208. User device 110 and/or system 130 may also include a network adapter or interface 216, such as a Transmission Control Protocol (TCP)/Internet Protocol (IP) adapter card or wireless communication adapter (such as a 4G wireless communication adapter using Orthogonal Frequency Division Multiple Access (OFDMA) technology). For example, application programs 211 may be downloaded to the computing device from an external computer or external storage device via a network (for example, the Internet, a local area network or other wide area network or wireless network) and network adapter or interface 216. From the network adapter or interface 216, the programs may be loaded onto computer readable storage media 208. The network may include copper wires, optical fibers, wireless transmission, routers, firewalls, switches, gateway computers and/or edge servers. User device 110 and/or system 130 may also include one or more output devices or interfaces 220 (e.g., a display screen), and one or more input devices or interfaces 222 (e.g., keyboard, keypad, mouse or pointing device, touchpad). For example, device drivers 212 may interface to output devices or interfaces 220 for imaging, to input devices or interfaces 222 for user input or user selection (e.g., via pressure or capacitive sensing), and so on. The device drivers 212, R/W drive or interface 214 and network adapter or interface 216 may include hardware and software (stored on computer readable storage media 208 and/or ROM 206).

System 130 can be a standalone network server or represent functionality integrated into one or more network systems. User device 110 and/or system 130 can be a laptop computer, desktop computer, specialized computer server, or any other computer system known in the art. In some embodiments, system 130 represents computer systems using clustered computers and components to act as a single pool of seamless resources when accessed through a network, such as a LAN, WAN, or a combination of the two. This embodiment may be desired, particularly for data centers and for cloud computing applications. In general, user device 110 and/or system 130 can be any programmable electronic device or can be any combination of such devices, in accordance with embodiments of the present disclosure.

The programs described herein are identified based upon the application for which they are implemented in a specific embodiment or embodiment of the present disclosure. That said, any particular program nomenclature herein is used merely for convenience, and thus the embodiments and embodiments of the present disclosure should not be limited to use solely in any specific application identified and/or implied by such nomenclature.

Embodiments of the present disclosure (e.g., especially those of Groups I-III) may be or use one or more of a device, system, method, and/or computer readable medium at any possible technical detail level of integration. The computer readable medium may include a computer readable storage medium (or media) having computer readable program instructions thereon for causing a processor to carry out one or more aspects of the present disclosure.

The computer readable (storage) medium can be a tangible device that can retain and store instructions for use by an instruction execution device. The computer readable medium may be, but is not limited to, for example, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire, in accordance with embodiments of the present disclosure.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform various aspects of the present disclosure. Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine or system, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks, in accordance with embodiments of the present disclosure.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Flowchart and block diagrams as shown in the drawings (see, e.g., FIGS. 5 and 6) illustrate at least some of the architecture, functionality, and operation of some embodiments of systems, methods, and computer readable media according to various embodiments of the present disclosure. In this regard, each block in the flowchart or block diagrams may represent a module, segment, or portion of instructions, which includes one or more executable instructions for implementing the specified logical function(s). In some embodiments, the functions noted in the blocks may occur out of the order noted in the Drawings. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be understood that although this disclosure includes a detailed description on cloud computing, embodiment of the teachings recited herein are not limited to a cloud-computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics can include: on-demand self-service: a cloud consumer can unilaterally provision computing capabilities, such as server time and network storage, as needed automatically without requiring human interaction with the service's provider; broad network access: capabilities are available over a network and accessed through standard mechanisms that promote use by heterogeneous thin or thick client platforms (e.g., mobile phones, laptops, and PDAs); resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter); rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time; measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows: software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings. Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows: private cloud: the cloud infrastructure is operated solely for an organization. It may be managed by the organization or a third party and may exist on-premises or off-premises. Community cloud: the cloud infrastructure is shared by several organizations and supports a specific community that has shared concerns (e.g., mission, security requirements, policy, and compliance considerations). It may be managed by the organizations or a third party and may exist on-premises or off-premises. Public cloud: the cloud infrastructure is made available to the general public or a large industry group and is owned by an organization selling cloud services. Hybrid cloud: the cloud infrastructure is a composition of two or more clouds (private, community, or public) that remain unique entities but are bound together by standardized or proprietary technology that enables data and application portability (e.g., cloud bursting for load-balancing between clouds). A cloud-computing environment is service oriented with a focus on statelessness, low coupling, modularity, and semantic interoperability. At the heart of cloud computing is an infrastructure that includes a network of interconnected nodes.

Figure 3:
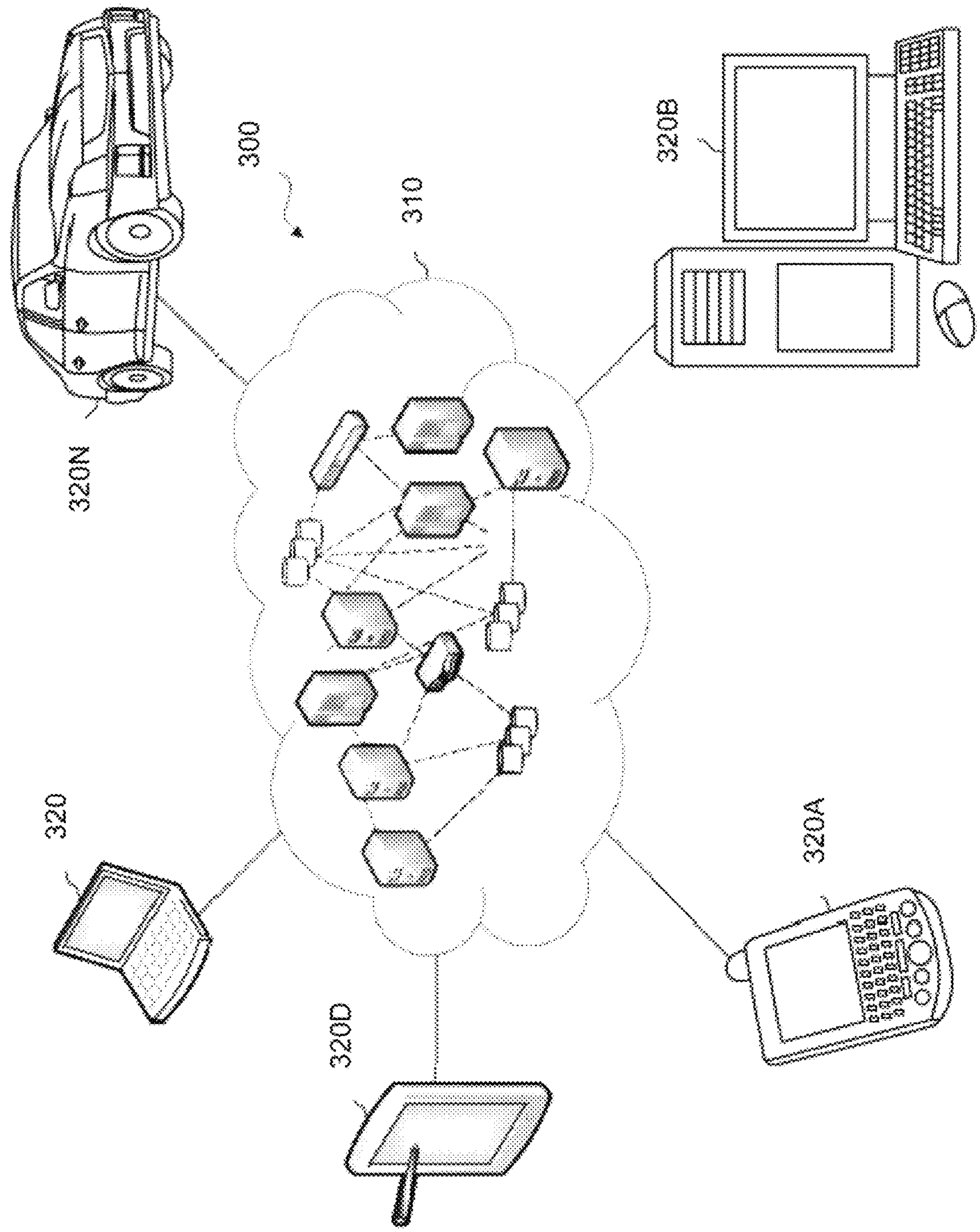
FIG. 3 depicts a cloud computing environment of the device/system for Groups I-III.

Referring now to FIG. 3, illustrative cloud computing environment 300 is depicted. As shown, cloud computing environment 300 includes one or more cloud computing nodes (not depicted) with which local computing devices used by cloud consumers, such as, for example, personal digital assistant (PDA) or cellular telephone 320A, desktop computer 320B, laptop computer 320C, and/or automobile computer system 320*n* may communicate. The one or more cloud computing nodes may communicate with one another. They may be grouped (not shown) physically or virtually, in one or more networks, such as Private, Community, Public, or Hybrid clouds as described hereinabove, or a combination thereof. This allows cloud-computing environment 300 may be implemented to offer infrastructure, platforms, and/or software as services for which a cloud consumer does not need to maintain resources on a local computing device. The types of computing devices 320A-N, as shown in FIG. 4, are intended to be illustrative only and that the one or more computing nodes and cloud computing environment 300 can communicate with any type of computerized device over any type of network and/or network addressable connection (e.g., using a web browser).

Figure 4:
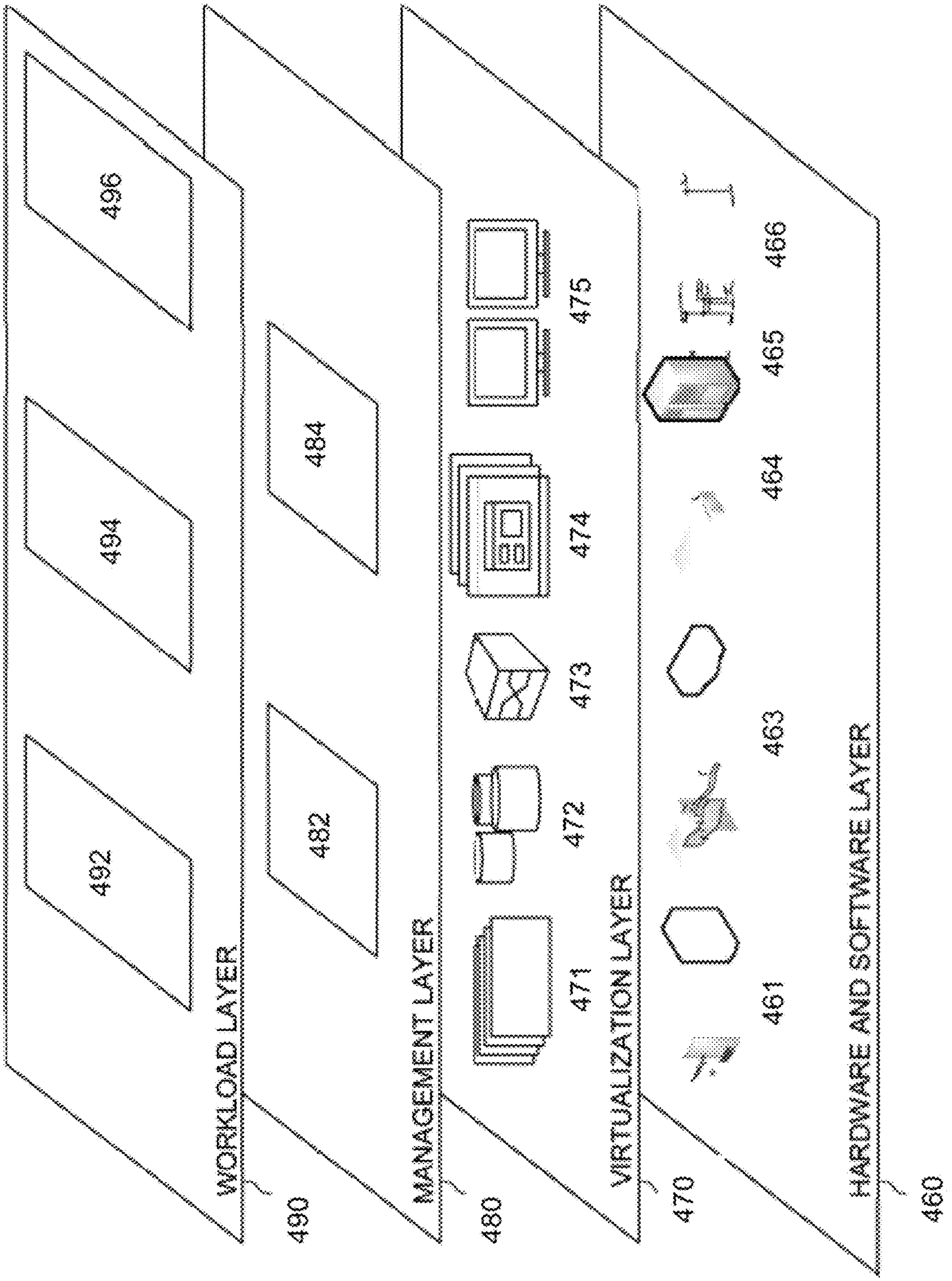
FIG. 4 depicts abstraction model layers of the device/system for the embodiments of Groups I-III.

Referring now to FIG. 4, a set of functional abstraction layers provided by cloud computing environment 300 is shown. The components, layers, and functions are intended to be illustrative only, and embodiments of the present disclosure are not limited thereto. As depicted, the following layers and corresponding functions are provided.

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468. Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

As an example, management layer 480 may provide the functions described below. Resource provisioning 481 provides dynamic procurement of computing resources and other resources that are utilized to perform tasks within the cloud-computing environment. Metering and Pricing 482 provide cost tracking as resources are utilized within the cloud-computing environment, and billing or invoicing for consumption of these resources. For example, these resources may include application software licenses. Security provides identity verification for cloud consumers and tasks, as well as protection for data and other resources. User portal 483 provides access to the cloud-computing environment for consumers and system administrators. Service level management 484 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 490 provides examples of functionality for which a cloud-computing environment (e.g., cloud computing environment 300) may be utilized. Examples of workloads and functions which may be provided from this layer include: navigation 491; software development and lifecycle management 492; virtual classroom education delivery 493; data analytics processing 494; transaction processing 495; and management 496. Management 496 may include functionality enabling the cloud-computing environment to be used to perform methodology according to any of the disclosed embodiments.

Group I Embodiments

Group I embodiments, pertain to systems, devices, and methods for market analytics and/or user recommendation of information (for example) to one or more users are provided. In such embodiments, the information corresponds to any one or more of media information (text/articles/publications, video, audio, combination thereof), products (any type of product, including financial products and stocks), and services, as well as other embodiments (e.g., see Summary and below). Specifically, Group I embodiments pertain generally to recommendations to one or more users of products/services/media/information/items base on an emotional impact factor.

With respect to embodiments for market analytics/user recommendation methods, such methodology includes identifying one or more correlations between at least one of one or more sentient agents and one or more non-sentient agents associated with corresponding systems, for example media platforms, and sales platforms, and the like. Additionally, such methodology includes determining at least one psychometric profile for each, the psychometric profile comprising an Emotional Impact Factor (EIF). Further, such methodology, in some embodiments, includes determining at least one market, and/or at least one recommendation using each EIF for at least one user. Thereafter, the at least one market and/or recommendation can be provided to at least one user.

Figure 5:
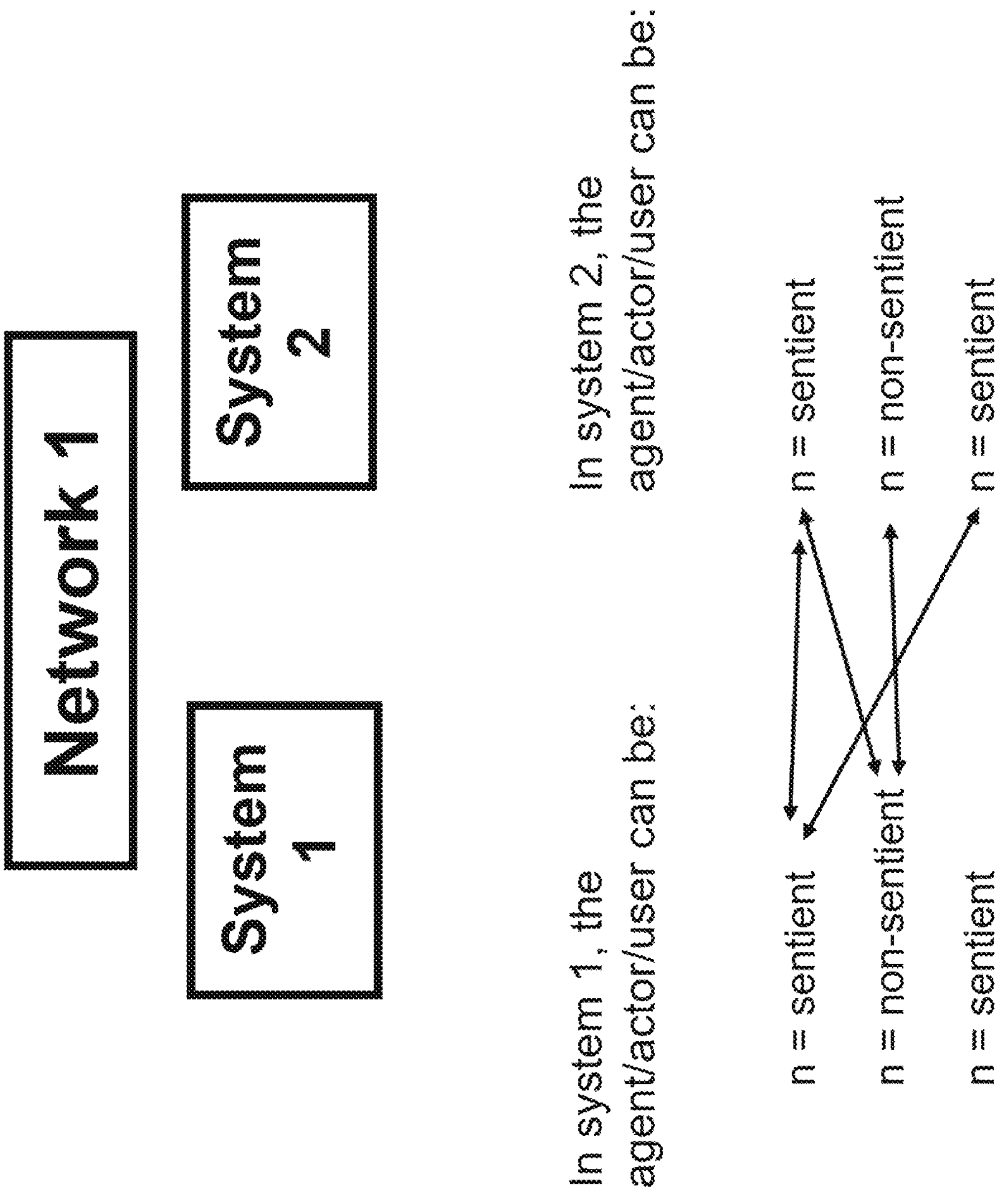
FIG. 5 is a block, schematic diagram of an overview of the methodology according to some embodiments of Group I.

To this end, FIG. 5, is a high-level overview of the methodology according to some embodiments. Accordingly, in the process of determining the EIF for actors/agents/entities (together "agents") in a plurality of networks (e.g., two) within a system. The agents can be either sentient or non-sentient. Matches are determined between structured and/or unstructured datasets, between hidden and visible layers (for example). Either network, as a whole (for example), can be sentient or non-sentient, as the process of determining EIF remains the same (according to some embodiments). An EIF can be understood, in the absence of a human actor, in terms of saturation or weighting. The factor that has the greatest weight within the network then replaces the equivalent of the strongest emotional factor.

For example, determining the EIF may comprise connecting a plurality of data points for identifying at least one parameter, such as, for example, data points associated with anthropological, ethnographic, and psychosocial factors. In some embodiments, determining the EIF includes integrating and/or weighting (according to methodology know to those skilled in the art) such one or more parameters, and/or integrating and/or weighting additional factors. Such additional factors include, for example, text-based analysis of annotations of information (e.g., of songs), indexing, media analysis, and principle component analysis. In some embodiments, determining the EIF may comprise or may further comprise examining structured or unstructured behavior data of a user or users. The structured and unstructured data may be from one or more defined networks and/or systems, where the defined networks and/or systems may comprise at least one of: streaming services, platforms (e.g., Netflix®, Hulu®, Amazon®), and peer-to-peer networks (together being referred to as "service(s)"). To this end, a respective EIF may be determined through an analysis of a limited number of parameter (e.g., in some embodiments $n>2$, $n>3$, $n>4$, $n>5$, $n>6$, $n>7$, $n>8$, $n>9$, $n>10$, $n>11$, or $n>12$ parameters).

The parameters include, for example, at least one of previous consumption within a given recommendation system and/or platform, and one or more peer-to-peer network transactions over a predetermined period of time. As noted above, such parameters/factors can be weighted, and in some embodiments, weighting is increased for transactions over the predetermined period of time.

The EIF, in some embodiments, may be configured for use for at least one of analyzing, visualizing, and recommending media content for at least one user, with the sentient agent configured to determine a relationship between at least one of a user's emotional quotient, psychometric profile, and the EIF of content available for consumption on a given media service.

In some embodiments, the EIF may be configured for use with a media recommendation system (e.g., publications, music, video), and may also be configured as a sales recommendation system configured to match at least one product to a user(s).

In some embodiments, a market analytics/user recommendation system is provided. Such a system, according to some embodiments, includes at least one processor having code operating thereon configured to cause the at least one processor to identify one or more correlations between at least one of one or more sentient agents and one or more non-sentient agents associated with corresponding systems, determine at least one psychometric profile for each, the psychometric profile comprising an Emotional Impact Factor (EIF), and determine at least one market, and/or at least one recommendation using each EIF for a user(s).

Such system embodiments (as well as others) may include one and/or another, and in some embodiments a plurality, and in some embodiments, structure and/or functionality for carrying out the foregoing methodology (for any such method embodiments) noted above. Moreover, some of the embodiments include devices, such as mobile devices (e.g., smartphones), running a mobile application which can work with system embodiments, such that, a user can receive recommendations on their mobile device (of course, mobile applications of service providers, media providers, streaming services can incorporate any of the above-noted functionality into their respective mobile applications). See General Embodiments above.

Some embodiments of the present disclosure are directed to systems, devices, and methods for a false-information/media (i.e., veracity) identification method. Such embodiments comprise reviewing one or more pieces of information/media, where each piece of media includes a source, determining at least one emotional impact factor (EIF) for each piece of media, and associating each EIF is a number or alphanumeric. The number or alphanumeric corresponds to a falseness scale, such that, in some embodiments, upon the associated EIF being greater than a predetermined threshold on the scale, the media may be flagged as false (or true, or presented to one or more users/viewers as a scale of veracity or falseness).

In some embodiments determination of the EIF may be configured for a specific audience, e.g., demographic. The audience or demographic may be one based on, for example, at least one of socio-economic status and educational level.

Such method embodiments may be embodied in a system comprising at least one processor having code operating thereon configured to cause the at least one processor to perform the methodology above. Such systems may be networked systems (e.g., via the internet) including one or more servers in communication with client/user computers accessing such systems to verify information/media.

Such system embodiments can further comprises a mobile application configured for operation on, used or in combination with a mobile application and/or device. Moreover, such a mobile application may be configured to at least one of send, receive, and/or process information from the at least one processor according to the disclosed system embodiments.

The veracity/falseness of reviewed information, in some embodiments, includes notifying a user(s)/consumer(s) of the one or more pieces of media of flagged false media, which can be done, via, for example, a user client computer, including, for example, a mobile device in wireless communication with the system. In addition to an in-application notification of the veracity of information, other forms of notification may be via text, phone, or email.

In some embodiments, the above-noted functionality can be incorporated into a media service's system, including, associated mobile applications.

Group II Embodiments

Embodiments of the present disclosure are directed to systems, devices, and methods for treating one or more brain functions, including neurological conditions and episodes associated therewith. Such embodiments determine OMM, which is hereinafter referred to as optimal medical media or OMM, which can be used to help treat a user suffering from a number of conditions associated with any number of brain functions, as well as being used for wellness. The OMM may be played through a user's audio/video device, including, for example, a smartphone operating a mobile application. Such embodiments can be configured to allay a fugue state, a panic attack, and achieve a dopaminergic state for a user.

Accordingly, in some embodiments, a brain function medical treatment method is provided, which can be performed by and/or in combination with a software system and/or application (and in some embodiments, a smartphone operating a mobile application) which determines one or more selections of the OMM. Such media comprises audio selections which are custom tailored to treat one or more brain functions, which may include neurological conditions and associated episodes thereof. Such OMM may be audio clips, segments (hereafter referred to as "pieces"), lasting from seconds, to minutes, to, in some embodiments, hours, and can be a single piece, or, a plurality of OMM pieces, which, in some embodiments, may be assembled together in one or more playlists. While some embodiments the OMM is audio content, in other embodiments, the OMM may be video content, or a combination of audio and video content.

In some embodiments, the OMM may comprise at least one song and includes a video component comprising lyrics corresponding to the at least one song configured such that the at least one user can sing the song. The OMM may also be selections derived or otherwise based on recorded compositions from Baroque, classical, and neoclassical periods, where the compositions may be augmented.

In some embodiments, the method includes (and associated system can be configured to) receiving first data corresponding to input from at least one patient (user) with respect to answers to a series questions (Q&A) regarding a brain function, or a condition or episode, corresponding to a brain function. In some embodiments, the questions are answered during a period when the user is not experiencing the condition or an associated episode. For example, such Q&A can include, for example, questions regarding anxiety, depression, etc. and variants within such as PTSD, and the like. Conditions can be, for example, weight issues (anorexia, obesity), concentration, anxiety disorders, distress, flow-state, general health, mood disorders, personality disorders, and stress; an episode can be, for example, a measurable or self-identified psychophysical disease or discomfort.

The method, in some embodiments, may also include selecting, by the user, one or more medical media parameters, or "MMP", which may comprise data associated with perspiration, heartrate, pulse, and/or other physiological response information, which can be used, in addition to the first data, to determine OMM for the user to help treat the condition or episode, and/or maintain wellness. In some embodiments, artificial intelligence (AI) may be used with at least one (and preferably both) of the first data and MMP, to determine the OMM. The AI may optionally comprise or include interaction with an AI bot (AIB), to aid in the identification of the OMM. The OMM is configured as a treatment or well-being plan for treating the episode or condition.

In some embodiments, the OMM is configured as at least one of one or more musical pieces, videos, and readings, which can then be configured into one or more playlists, each of which can be customized to treat (i.e., via playing and listening to the OMM via a media player such as a smartphone) a particular condition, disorder, and/or associated episode, as well as customized to maintain wellness (e.g., meditation).

For example, inspirational songs (e.g., songs about journeys, loving, and kindness) can be selected based on a user's particular tastes (which is determined based on at least one of the information garnered from the Q&A, and in some embodiments, the AI/AIB selections. Such AI/AIB selections may be trained based on at least one of the Q&A information, additional follow-up Q&A information (e.g., feedback information on previous playlist selections made by the system), secondary information (see below) or other information training sets (e.g., selected by medical/psychiatric professionals).

The OMM (including any configured playlists) can include a guiding component, which may be a medical professional voiceover (or AIB voiceover), guiding the user playing the OMM/playlist through the music, and/or managing the user through the treatment of the condition/disorder, or wellness (e.g., meditation).

A playlist may comprise a plurality of playlists each corresponding to a type including one or more of the following characteristics for the OMM of the playlist: variation of time signature, absence of minor keys, organic instrumentation, variation of instrumentation, absence of dissonance, balanced audio recording, limitation of decibel level, pre-set decibel level, familiarity, length of play, continuous play, intermission length, dopaminergic effect, and anxiolytic effect.

As noted above, the user (and/or medical/wellness professional) can provide feedback information into the system so as to not only train the AI/AIB for improved OMM selections for a particular user, but also to determine the efficacy of the OMM (e.g., efficacy can be determined for the OMM over a defined longitudinal application (e.g., measurable wellness, as a personalized medical tool). In some embodiments, the method/system can track secondary information, including, for example, health data, and personal data. The health data may comprise at least one of heartrate, blood pressure, and temperature, the personal data may comprise at least one of caloric intake, exercise/activity data, sleep data, medications, and fluid intake data. In some embodiments, reports can be produced which can list at least one of (and preferably several of or all of) data input, OMM selections, efficacy determination, feedback information, and the like.

In some embodiments, the system can be configured to identify an emergency or potential emergency, by determining aberrations in user-behavior, as well as to recognize patterns for a user so as to identify trends in the at least one user with respect to selection of specific words indicative of a condition for an associated brain function. In some embodiments, the system can be configured to determining using, for example, at least the secondary information, whether the user is within or outside of a state (e.g., a flow state, an emergency state).

The system may also be configured to notify at least one of the user and one or more individuals associated with the at least one user, e.g. regarding the at least one user having experienced or experiencing an episode, is suffering from a condition, and/or is within or outside of a state (which can utilize secondary information). Notification can be at least one of email, text, phone, and/or any method of secure direct in-application communication (e.g., notification, alert).

In some embodiments, the system may be configured to include an account for each user, accessible via a website, or via a mobile application. Such a system may be established such that use is paid for via, for example, advertisement, and/or, via traditional payments via user direct funding (e.g., credit card), or insurance. Funds may be collected/aggregating for each account from a third party (e.g., an insurance provider). In addition use (of funds) can be incentivized via the sale of data collected, analyzed, and/or otherwise produced (by system analyzation, AI, etc.).

In some embodiments, the system may be configured to select OMM so as to direct or otherwise train a user to develop new habits through behavior modification. Such training may include any (or at least one) of: centering, practicing neuro-feedback, and mindfulness, then returning to a state of productivity; delaying a length of time treatment of the at least one of the neurological episode and condition.

In some embodiments, the OMM may be manipulated by at least one of the at least one user, a medical professional, and via AI. For example, using AI, one or more STEMs associated with one or more pieces of the OMM can be produced (the OMM itself may comprise one or more STEMs). Such modifications may include, for example, manipulating the key of the OMM, and/or remixing a STEM(s) associated with the OMM.

Each STEM may correspond to a core element to an OMM piece/selection, and in some embodiments, comprise digital recordings of individual instruments, or a combination of instruments, or mixes thereof, for example, of a plurality of individual recorded tracks. For example, a percussion STEM can be a digital audio file of a bass drum, or a combination of different individual drums/components of a drum set (e.g., snare drum, cymbal, hi-hat, tom-tom, etc.), that when played, sounds like a complete drum set. A STEM may also be a particular song, or selection of music (e.g., Beethoven's Symphony No. 5 in C minor Op. 67).

In some embodiments, unique STEMs are created for particular OMM by training AI to manipulate, edit (e.g., content, length), and/or otherwise modified new or existing STEMs to customize them to treat or further a particular brain function (or condition, or episode associated therewith, or wellness). For example, each STEM can have an initial configuration with respect to tone, effects, compression, equalization, key and the like, perhaps for a particular brain function or condition. Individual STEMs can be so modified, and then mixed together to form yet further STEMs. The system, as noted above, may be configured to modify the STEMs and combine two or more, etc., to produce OMM for the particular brain function/condition/episode for treatment. STEMs may also be referred to as mixes (i.e., audio and/or video tracks, processed separately prior to combining them into a master mix or master STEM. A STEM may also be referred to as sub-mix, a sub-group, or a bus.

For the AI to modify a STEM(s), a user can select at least one parameter, and then the AI can compose one or more pieces of the OMM by mixing/re-mixing one or more STEMs associated with the OMM (for example). The AI can be trained to manipulate previously produced (and stored) and new STEMs so as to determine OMM for a particular user for a particular brain function (condition and/or episode associated therewith). Thus, in some embodiments, the determined OMM (and corresponding playlist(s)) can be configured by the system to interact with one another to produce a desired affect.

In some embodiments, a brain function medical treatment system is provided and comprises or otherwise includes at least one processor having code operating thereon configured to cause the at least processor to conduct the above noted steps for methods to treat one or more brain functions, conditions corresponding thereto, and episodes associated therewith, with OMM. The at least one processor may comprise one or more servers, and/or computers, as well as a mobile application for users (and in some embodiments, administrators of the system) to make use of the OMM. Such a mobile application may be configured to at least one of send, receive, and/or process information from the at least one processor.

In some embodiments, the system is established a set of stored STEMs for producing the OMM for users; such stored STEMs may also be referred to as core STEMs. From this, using information provided by the user, a medical professional, and/or AI, OMM is determined for a user for a brain function/condition, and then preferably assembled into a playlist. Particularly, in some embodiments, AI is used to modify one or more of the stored STEMS so as to customize it for a particular user and for a particular brain function/condition.

Figure 6:
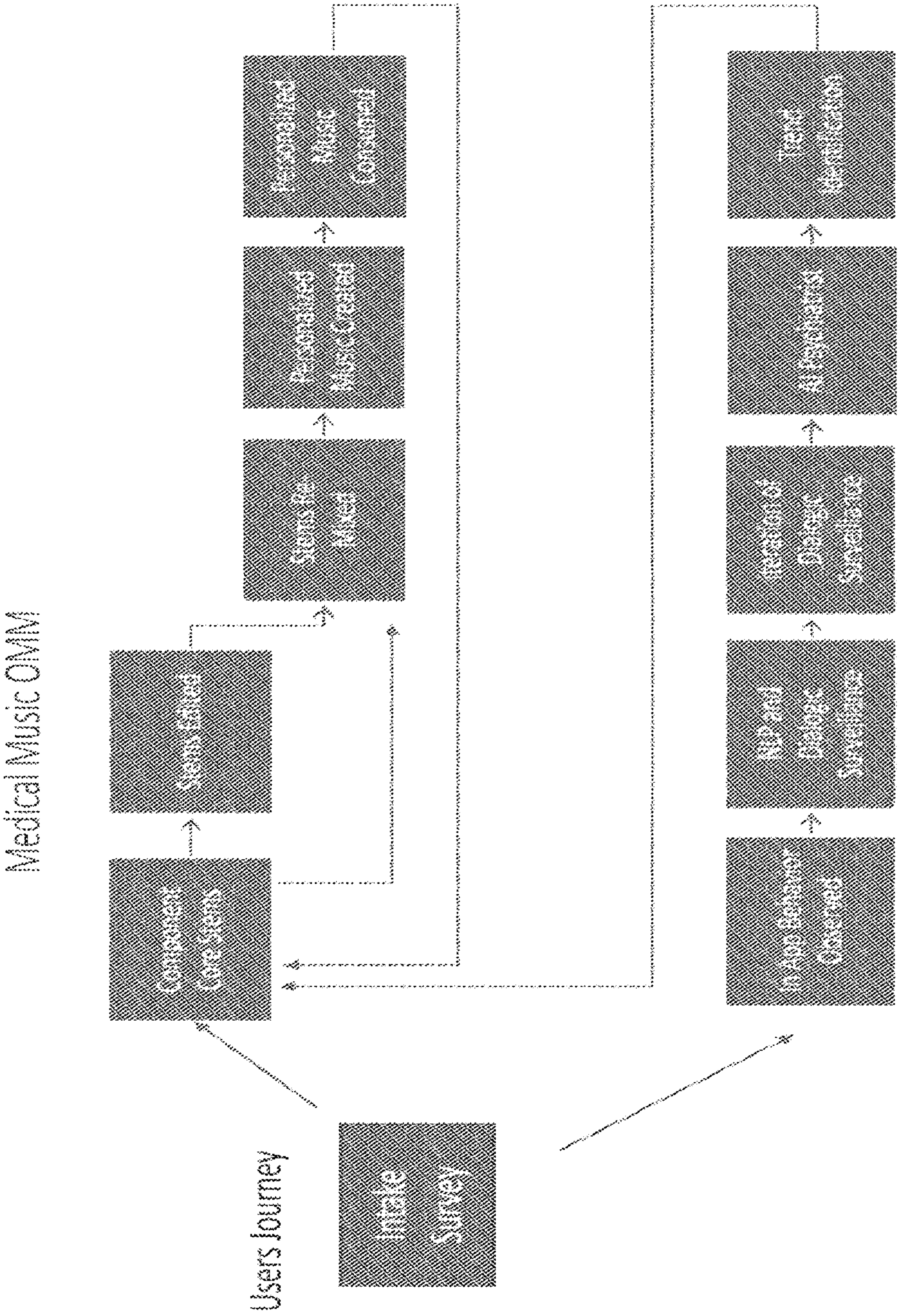
FIG. 6 is a block, schematic diagram of an overview of the methodology according to some embodiments of Group II.

FIG. 6 illustrates a flow diagram depicting an exemplary process according to some embodiments. As shown, a user seeking treatment may first answer questions for a survey or questionnaire via a mobile application regarding a brain function or condition that the user wishes to seek treatment. From the answers which are uploaded into the system (e.g., a server), and component core STEMs are selected. In view of the answers provided, the selected STEMs are then modified and or edited and/or modified so as to be customized for the particular user and condition. Thereafter, the STEMs are then remixed which results in OMM ("Personalized Music Created"), and then used by the user (e.g., via a smartphone application). The OMM and associated STEMs can be stored and become core STEMs.

The mobile application which plays the OMM for the user may also be configured to monitor user behavior and store and/or upload data associated with such behavior to the server. The mobile application may also interact in real-time (or near real-time, "real-time" is hereinafter any communication or event that happens in current time or near current time) with AI, or the AIB, via spoken or typed responses; in some embodiments, such user behavior may be monitored in real-time via the sensors provided in the smartphone/mobile device that the mobile application is operating. Through natural language processing (NLP/dialogic), the spoken and monitored behavior is interpreted by the AIB, and the AIB can respond via typed or spoken word (e.g., using Siri, for example, in IOS® devices).

By use and repetitive use of the OMM and refined OMM determined by the system and used by the user, the AI/AIB identify trends. Such trends can then be used in future iterations of OMM selections for the particular user, or other users having similar personality trains/survey answers who are seeking like treatment.

While various inventive embodiments have been described and illustrated herein, those having ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all structure, parameters, dimensions, materials, functionality, and configurations described herein are meant to be an example and that the actual structure, parameters, dimensions, materials, functionality, and configurations will depend upon the specific application or applications for which the inventive teachings is/are used.

Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the claims supported by the present disclosure, and equivalents thereto, inventive embodiments may be practiced otherwise than as specifically described and claimed. Inventive embodiments of the present disclosure are also directed to each individual feature, system, article, structure, material, kit, functionality, step, and method described herein. In addition, any combination of two or more such features, systems, articles, structure, materials, kits, functionalities, steps, and methods, if such are not mutually inconsistent, is included within the inventive scope of the present disclosure. Some embodiments may be distinguishable from the prior art for specifically lacking one or more features/elements/functionality (i.e., claims directed to such embodiments may include negative limitations).

Also, as noted, various inventive concepts are embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terminology used herein was chosen to best explain the principles of the one or more embodiments, practical applications, or technical improvements over current technologies, or to enable understanding of the embodiments disclosed herein. As described, details of well-known features and techniques may be omitted to avoid unnecessarily obscuring the embodiments of the present disclosure.

References in the specification to "one embodiment," "an embodiment," "an example embodiment," or the like, indicate that the embodiment described may include one or more particular features, structures, or characteristics, but it shall be understood that such particular features, structures, or characteristics may or may not be common to each and every disclosed embodiment of the present disclosure herein. Moreover, such phrases do not necessarily refer to any one particular embodiment per se. As such, when one or more particular features, structures, or characteristics is described in connection with an embodiment, it is submitted that it is within the knowledge of those skilled in the art to affect such one or more features, structures, or characteristics in connection with other embodiments, where applicable, whether or not explicitly described.

What is currently claimed:

1. A brain function medical treatment method, comprising:

determining optimal medical media (OMM) configured to counteract at least one user experiencing a condition from entering at least one state associated with the condition, wherein the OMM is determined based on data corresponding to brain function of the user collected when the user is outside the at least one state, wherein the OMM is at least partially configured using artificial intelligence;

selecting a plurality of STEMs based on the determined OMM, wherein each STEM is a digital audio file;

producing the OMM by remixing the plurality of STEMs; and treating the at least one user by causing the identified OMM to be played to the at least one user.

2. The method of claim 1, wherein:

the OMM is configured as at least one playlist, wherein each playlist includes a plurality of portions of audio, wherein each playlist has at least one characteristic defined with respect to audio of the playlist.

3. The method of claim 1, wherein:

the condition is selected from the group consisting of: distress, flow-state, weight-loss, and concentration.

4. The method of claim 1, further comprising:

obtaining feedback data on use of the OMM for treatment of the at least one condition; and training an artificial intelligence model to configure the OMM for the at least one user based on the feedback data.

5. The method of claim 1, further comprising:

training an artificial intelligence model using at least one of user-selected parameters, feedback information, secondary information, and medication information;

identifying an emergency based on aberrations in user-behavior of the at least one user;

recognizing patterns for the at least one user with respect to selection of words indicative of a neurological condition, wherein the at least one user is treated with respect to the neurological condition.

6. The method of claim 1, further comprising:

causing the at least one user to develop new habits through behavior modification via the OMM, wherein causing the at least one user to develop new habits includes at least one activity then returning to a state of productivity.

7. The method of claim 1, wherein treating the user causes any of: allay of a fugue state, allay of a panic attack, and achievement of a dopaminergic state.

8. The method of claim 1, wherein the OMM is generated by an artificial intelligence model, wherein the artificial intelligence model is trained to modify at least a portion of the plurality of STEMs with respect to the condition.

9. The method of claim 8, wherein the artificial intelligence model is configured to generate the OMM by modifying at least one of the plurality of STEMs.

10. The method of claim 1, wherein the OMM further includes at least one video track corresponding to at least a portion of audio of the plurality of STEMs.

* * * * *